United States Patent
Lee et al.

(10) Patent No.: US 10,144,809 B2
(45) Date of Patent: Dec. 4, 2018

(54) METHOD FOR PREPARING SUPER ABSORBENT POLYMER AND SUPER ABSORBENT POLYMER PREPARED THEREBY

(71) Applicant: LG Chem, Ltd., Seoul (KR)

(72) Inventors: Seung Mo Lee, Daejeon (KR); Gi Cheul Kim, Daejeon (KR); Kum Hyoung Lee, Daejeon (KR); Se Yeol Park, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/313,202

(22) PCT Filed: Dec. 10, 2015

(86) PCT No.: PCT/KR2015/013530
§ 371 (c)(1),
(2) Date: Nov. 22, 2016

(87) PCT Pub. No.: WO2016/111473
PCT Pub. Date: Jul. 14, 2016

(65) Prior Publication Data
US 2017/0198105 A1  Jul. 13, 2017

(30) Foreign Application Priority Data
Jan. 6, 2015  (KR) .................. 10-2015-0001285

(51) Int. Cl.
| | | |
|---|---|---|
| *A61F 13/53* | (2006.01) | |
| *A61L 15/60* | (2006.01) | |
| *B01J 20/26* | (2006.01) | |
| *C08F 2/10* | (2006.01) | |
| *C08F 2/44* | (2006.01) | |
| *C08F 20/06* | (2006.01) | |
| *C08J 3/00* | (2006.01) | |
| *C08J 3/075* | (2006.01) | |
| *C08J 3/12* | (2006.01) | |
| *C08J 3/24* | (2006.01) | |

(52) U.S. Cl.
CPC ............... *C08J 3/005* (2013.01); *A61F 13/53* (2013.01); *A61L 15/60* (2013.01); *B01J 20/26* (2013.01); *B01J 20/267* (2013.01); *C08F 2/10* (2013.01); *C08F 2/44* (2013.01); *C08F 20/06* (2013.01); *C08J 3/075* (2013.01); *C08J 3/12* (2013.01); *C08J 3/24* (2013.01); *C08J 3/245* (2013.01); *B01J 2220/68* (2013.01); *C08F 2810/20* (2013.01); *C08J 2333/02* (2013.01); *C08J 2433/00* (2013.01)

(58) Field of Classification Search
CPC .... C08F 2/10; C08F 2/44; C08F 20/06; C08F 2810/20; C08J 3/005; C08J 3/075; C08J 3/12; C08J 3/24; C08J 3/245; C08J 2333/02; C08J 2433/00; B01J 20/26; B01J 20/267; B01J 2220/68; A61F 13/53; A61F 15/60
See application file for complete search history.

(56) References Cited

U.S. PATENT DOCUMENTS

| | | |
|---|---|---|
| 4,446,261 A | 5/1984 | Yamasaki et al. |
| 5,185,385 A | 2/1993 | Kanluen et al. |
| 2005/0136023 A1 | 6/2005 | Yahiaoui et al. |
| 2006/0252913 A1 | 11/2006 | Herfert et al. |
| 2008/0045624 A1 | 2/2008 | Losch et al. |
| 2008/0081848 A1 | 4/2008 | Shih et al. |

FOREIGN PATENT DOCUMENTS

| | | |
|---|---|---|
| CN | 101914213 A | 12/2010 |
| CN | 102336861 A | 2/2012 |
| JP | S56161408 A | 12/1981 |
| JP | S57158209 A | 9/1982 |
| JP | 57-198714 A | 12/1982 |
| JP | 20000026510 A | 1/2000 |
| JP | 2002105125 A | 4/2002 |
| JP | 2008007601 A | 1/2008 |
| KR | 20120047034 A | 5/2012 |
| KR | 20140036866 A | 3/2014 |
| KR | 20140065591 A | 5/2014 |

OTHER PUBLICATIONS

International Search Report from PCT/KR2015/013530, dated Jun. 3, 2016.
Odian, George, "Principles of Polymerization." Second Edition, John Wiley & Sons, 1981, p. 203.
Schwalm, Reinhold, "UV Coatings: Basics, Recent Developments and New Applications." Elsevier Science, Dec. 21, 2006, p. 115.
Extended European Search Report for Application No. EP15877193.1 dated Dec. 12, 2017.

*Primary Examiner* — Irina S Zemel
*Assistant Examiner* — Jeffrey S Lenihan
(74) *Attorney, Agent, or Firm* — Lerner, David, Littenberg, Krumholz & Mentlik, LLP

(57) ABSTRACT

The present invention relates to a method for preparing super absorbent polymer, and the method for preparing super absorbent polymer according to the present invention may reduce the content of non-reacted monomers in the super absorbent polymer, by using three kinds of polymerization initiators.

18 Claims, No Drawings

METHOD FOR PREPARING SUPER ABSORBENT POLYMER AND SUPER ABSORBENT POLYMER PREPARED THEREBY

CROSS-REFERENCE TO RELATED APPLICATION(S)

The present application is a national phase entry under 35 U.S.C. § 371 of International Application No. PCT/KR2015/013530, filed Dec. 10, 2015, published in Korean, which claims priority from Korean Patent Application No. 10-2015-0001285 filed on Jan. 6, 2015, the disclosures of which are herein incorporated by reference in their entirety.

TECHNICAL FIELD

The present invention relates to a method for preparing super absorbent polymer that can reduce the content of non-reacted monomers in the super absorbent polymer, and super absorbent polymer prepared thereby.

BACKGROUND OF ART

Super absorbent polymer (SAP) is a synthetic polymer material capable of absorbing moisture from about 500 to about 1,000 times its own weight, and it has been also called a super absorbency material (SAM), an absorbent gel material (AGM) and so on. Such super absorbent polymers started to be practically applied in sanitary products, and now they are widely used for preparation of various products, for example, hygiene products such as disposable diapers for children, water retaining soil products for gardening, water stop materials for the civil engineering and construction, sheets for raising seedling, fresh-keeping agents for food distribution fields, or the like.

The known preparation process for such super absorbent polymers includes a process by reverse phase suspension polymerization and a process by aqueous solution polymerization. Among them, the process by reverse phase suspension polymerization is disclosed in Japanese Laid-Open Patent Publication No. Sho 56-161408, Japanese Laid-Open Patent Publication No. Sho 57-158209, and Japanese Laid-Open Patent Publication No. Sho 57-198714, and the like. And, the process by aqueous solution polymerization includes a thermal polymerization method in which a hydrous gel phase polymer is polymerized while being broken and cooled in a kneader equipped with a plurality of shafts, and a photo-polymerization method in which an aqueous solution of a high concentration is irradiated by UV and the like on a belt to simultaneously progress polymerization and drying.

Meanwhile, absorption speed, which is one of the important properties of super absorbent polymer, is related to surface dryness of a product contacting skin such as a diaper. In general, the absorption speed may be improved by increasing the surface area of super absorbent polymer.

For example, a method of forming a porous structure on the surface of super absorbent polymer particles using a blowing agent is applied. However, with common blowing agents, a sufficient amount of a porous structure cannot be formed, and thus, increase rate of the absorption speed is not high.

For another example, a method of reassembling fine particles obtained in the preparation process of super absorbent polymer to form porous particles of irregular shapes, thus increasing the surface area is used. However, although the absorption speed of super absorbent polymer may be improved by this method, centrifuge retention capacity (CRC) and absorbency under pressure (AUP) of the polymer are relatively lowered. As such, since the properties of absorption speed, centrifuge retention capacity, absorbency under pressure, and the like of super absorbent polymer have trade-off relationship, a preparation method capable of simultaneously improving these properties is urgently needed.

Meanwhile, since the monomers used for the preparation of super absorbent polymer are strong acid, they have adverse effects on the human body such as skin irritation with a small amount, and thus, it is important to reduce the content of non-reacted monomers in the super absorbent polymer.

Since gel type super absorbent polymer is prepared as monomers are polymerized, non-reacted monomers remain inside the gel, and thus, it is difficult to physically or chemically remove them after polymerizing super absorbent polymer. Thus, a method of increasing the amount of polymerization initiators when polymerizing monomers to polymerize all the monomers as possible is conventionally used. However, this method has problems in that as reaction sites increase, the strength of the polymer network of super absorbent polymer decreases, thus decreasing absorption property, and in that due to the use of excessive polymerization initiators, discoloration of super absorbent polymer appears.

Thus, the inventors, during the assiduous studies on the preparation method of super absorbent polymer capable of reducing the content of non-reacted monomers in the super absorbent polymer, confirmed that the preparation method as explained below can fulfill the above requirement, and completed the invention.

DETAILED DESCRIPTION OF THE INVENTION

Technical Problem

It is an object of the invention to provide a method for preparing super absorbent polymer capable of reducing the content of non-reacted monomers in the super absorbent polymer, and super absorbent polymer prepared thereby.

Technical Solution

In order to solve the object, the present invention provides a method for preparing super absorbent polymer, comprising the steps of:

1) polymerizing a monomer composition comprising a water soluble ethylene-based unsaturated monomer, a photopolymerization initiator, a first thermal polymerization initiator with a decomposition temperature of 40 to 120° C., and a second thermal polymerization initiator with a decomposition temperature of 120 to 250° C. to prepare a hydrous gel phase polymer, 2) drying the hydrous gel phase polymer, and 3) milling the dried polymer.

Since the monomers used for the preparation of super absorbent polymer are strong acid, they causes adverse effects on the human body such as skin irritation and the like with a small amount, and thus, it is important to reduce the content of non-reacted monomers in the super absorbent polymer. Thus, in the present invention, three kinds of polymerization initiators are used as described above, and each polymerization initiator is sequentially decomposed in the polymerization and drying steps to progress polymerization reactions, thus reducing the content of non-reacted monomers in the finally prepared super absorbent polymer.

Hereinafter, the present invention will be explained in detail according to each step.

Step of preparing a hydrous gel phase polymer (step 1)
First, the method for preparing super absorbent polymer comprises the step of polymerizing a monomer comprising a water soluble ethylene-based unsaturated monomers to prepare a hydrous gel phase polymer.

The water soluble ethylene-based unsaturated monomers included in the monomer composition may be any monomers commonly used for the preparation of super absorbent polymer. As a non-limiting example, the water soluble ethylene-based unsaturated monomer may be a compound represented by the following Chemical Formula 1:

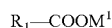  [Chemical Formula 1]

in the Chemical Formula 1,
$R^1$ is an alkyl group containing an unsaturated bond and having 2 to 5 carbon atoms, and
$M^1$ is a hydrogen atom, a monovalent or divalent metal, an ammonium group, or an organic amine salt.

Preferably, the monomer may be one or more selected from the group consisting of acrylic acid, methacrylic acid, and monovalent metal salts, divalent metal salts, ammonium salts and organic amine salts thereof. As such, in case acrylic acid or a salt thereof is used as the water soluble ethylene-based unsaturated monomer, super absorbent polymer having improved absorbency may be obtained, which is advantageous. Besides, as the monomers, maleic anhydride, fumaric acid, crotonic acid, itaconic acid, 2-acryloylethane sulfonic acid, 2-methacryloylethane sulfonic acid, 2-(metha)acryloylpropane sulfonic acid, 2-(meth)acrylamide-2-methyl propane sulfonic acid, (meth)acrylamide, N-substituted (meth)acrylate, 2-hydroxyethyl(meth)acrylate, 2-hydroxypropyl (meth)acrylate, methoxypolyethyleneglycol (meth)acrylate, polyethyleneglycol (meth)acrylate, (N,N)-dimethylaminoethyl (meth)acrylate, (N,N)-dimethylaminopropyl (meth)acrylamide, and the like may be used.

Wherein, the water soluble ethylene-based unsaturated monomers may have an acidic group, at least a part of which is neutralized. Preferably, the monomers partially neutralized with alkali material such as sodium hydroxide, potassium hydroxide, ammonium hydroxide and the like may be used.

Wherein, the polymerization degree of the monomers may be 40 to 95 mol %, or 40 to 80 mol %, or 45 to 75 mol %. Although the range of the polymerization degree may vary according to the final properties, if the polymerization degree is too high, neutralized monomers may be precipitated, thus rendering it difficult to smoothly progress polymerization, and to the contrary, if the polymerization degree is too low, absorption force of the polymer may be significantly lowered, and it may exhibit elastic rubber-like properties, which is difficult to handle.

And, the concentration of the water soluble ethylene-based unsaturated monomers in the monomer composition may be appropriately controlled considering polymerization time and reaction conditions and the like, and preferably, it may be 20 to 90 wt %, or 40 to 65 wt %. Such a concentration range makes it unnecessary to remove non-reacted monomers after polymerization using gel effect which appears in the polymerization reaction of an aqueous solution of high concentration, and yet, it may be advantageous for controlling milling efficiency when milling polymer as described below. However, if the concentration of the monomers becomes too low, the yield of super absorbent polymer may decrease. To the contrary, if the concentration of the monomers becomes too high, a part of the monomers may be precipitated or milling efficiency when milling hydrous gel phase polymer may be lowered, thus causing process problems, and the properties of the super absorbent polymer may be degraded.

The monomer composition may comprise polymerization initiators, and the present invention is characterized by comprising three kinds of polymerization initiators of a photopolymerization initiator, a first thermal polymerization initiator, and a second thermal polymerization initiator.

First, the photopolymerization initiator used in the present invention means material that can be decomposed by a certain amount of heat generated by UV irradiation and the like, to form radicals. However, it includes material that can be decomposed by heat directly provided by heating and the like, other than UV irradiation.

As examples of the photopolymerization initiator, one or more compound selected from the group consisting of benzoin ether, dialkyl acetophenone, hydroxyl alkylketone, phenyl glyoxylate, benzyl dimethyl ketal, acyl phosphine and α-aminoketone may be used. As a specific example of the acyl phosphine, corresponding lucirin TPO, namely, 2,4,6-trimethyl-benzoyl-trimethyl phosphine oxide may be used. Various photo polymerization initiators are disclosed in Reinhold Schwalm, "UV Coatings: Basics, Recent Developments and New Application (Elsevier 2007)", page 115.

To the monomer composition, UV and the like are irradiated or a certain amount of heat is added to progress a polymerization reaction, and since the polymerization reaction is an exothermic reaction, the temperature of the reaction system increases. Thereby, if the temperature of the reaction system reaches the decomposition temperature of the first thermal polymerization initiator, the first thermal polymerization initiator is decomposed to form radicals, thus additionally progressing polymerization with non-reacted monomers. The first thermal polymerization initiator may be decomposed to form radicals at 40 to 120° C., or 50 to 110° C., or 40 to 100° C. The decomposition temperature may be measured using water as a solvent, as a temperature at which the polymerization of the monomer composition initiates.

Examples of the first thermal polymerization initiator may include persulfate-based initiators such as sodium persulfate ($Na_2S_2O_8$), potassium persulfate ($K_2S_2O_8$), ammonium persulfate (($NH_4$)$_2S_2O_8$), and the like; and azo-based initiators such as 2,2-azobis(2-amidinopropane) dihydrochloride, 2,2-azobis-(N,N-dimethylene)isobutyramidine dihydrochloride, 2-(carbamoylazo)isobutylonitril, 2,2-azobis[2-(2-imidazolin-2-yl)propane] dihydrochloride, 4,4-azobis-(4-cyanovaleric acid), and the like. For more various thermal polymerization initiators, Odian, "Principle of Polymerization (Wiley, 1981)", page 203 may be referred to.

And, in addition to the photo polymerization initiator and the first thermal polymerization initiator, the monomer composition comprises a second thermal polymerization initiator. Since the temperature of the reaction system cannot reach the decomposition temperature of the second thermal polymerization initiator in the above polymerization reaction, the second thermal polymerization initiator remains as it is without being decomposed in the Step 1, and is decomposed by heat added in the drying step of the Step 2 as described below, to form radicals, thus additionally progressing polymerization with non-reacted monomers. The second thermal polymerization initiator may be decomposed to form radicals at 120 to 250° C., or 150 to 200° C., or 160 to 180° C. The decomposition temperature may be measured using water as a solvent, as a temperature at which the polymerization of the monomer composition initiates.

As the second thermal polymerization initiator, the compound represented by the following Chemical Formula 2 may be used:

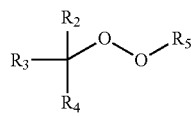

[Chemical Formula 2]

wherein $R_2$ and $R_3$ are each independently $C_{1-4}$ alkyl, $R_4$ is $C_{1-4}$ alkyl, $C_{3-6}$ cycloalkyl, or $C_{3-6}$ cycloalkyl substituted with $C_{1-4}$ alkyl, $R_5$ is hydrogen, or $CR_6R_7R_8$, $R_6$ and $R_7$ are each independently $C_{1-4}$ alkyl, and $R_8$ is $C_{1-6}$ alkyl, $C_{1-6}$ alkyl substituted with $C_{1-4}$ alkylperoxy, or $C_{6-10}$ aryl.

Since at least one carbon substituted with peroxy is tertiary carbon in the compound represented by the Chemical Formula 2, in order to decompose oxygen-oxygen bond, relatively high energy is required compared to the first thermal polymerization initiator. Thus, the compound represented by the Chemical Formula 2 remains as it is without being decomposed in the Step 1, and is decomposed by heat added in the drying step of the Step 2 as described below.

In the Chemical Formula 2, preferably, $R_2$ and $R_3$ are methyl.

And, preferably, $R_4$ is tert-butyl, hexyl, or hexyl substituted with methyl (for example, 4-methyl-hexyl).

And, preferably, $R_6$ and $R_7$ are methyl.

And, preferably, $R_8$ is methyl, isopentyl substituted with tert-butylperoxy (for example, 3-tert-butyl peroxyisopentyl), or phenyl.

Specific examples of the compound represented by the Chemical Formula 2 may include 2,5-dimethyl-2,5-bis(tetrabutylperoxy)hexane, tert-butyl hydroperoxide, tert-butyl cumyl peroxide, di-tert-butyl peroxide, or p-menthane hydroperoxide.

The compound represented by the Chemical Formula 2 may be prepared by an organic synthetic method commonly used in the art, or may be commercially purchased.

As explained, by using three kinds of polymerization initiators, as temperature rises in the polymerization process, the photopolymerization initiator and the first thermal polymerization initiator are sequentially decomposed to progress polymerization, thus reducing the amount of non-reacted monomers. And, since non-reacted monomers remaining after the polymerization step are additionally polymerized by the second thermal polymerization initiator in the drying step, the amount of non-reacted monomers in the finally prepared super absorbent polymer may be greatly reduced.

The three kinds of polymerization initiators may be added in the concentration of about 0.001 to 1 wt % to the monomer composition. That is, if the concentration of the polymerization initiators is too low, polymerization speed may become slow, and remaining monomers may be extracted in large quantities in the final product. To the contrary, if the concentration of the polymerization initiators is too high, a polymer chain making up a network may become short, and thus, the content of water soluble components may increase and absorbency under pressure may decrease, thus degrading the properties of the polymer.

And, it is preferable that the weight ratio of the three kinds of polymerization initiators (photo polymerization initiator: a first thermal polymerization initiator: a second thermal polymerization initiator) may be 1:7-15:3-10.

Meanwhile, the monomer composition may further comprise a cross linking agent ("internal cross linking agent") for improving the properties of the polymer by the polymerization of the water soluble ethylene-based unsaturated monomers. The cross linking agent is to internally cross link hydrous gel phase polymer, and may be used separately from the cross linking agent ("surface cross linking agent") for cross linking the surface of the hydrous gel phase polymer.

As the internal cross linking agent, any compounds may be used as long as it enables the introduction of cross-linked bond when polymerizing the water soluble ethylene-based unsaturated monomers. As non-limiting examples, multi-functional cross linking agents such as N,N'-methylenebisacrylamide, trimethylolpropane tri(meth)acrylate, ethyleneglycol di(meth)acrylate, polyethyleneglycol (meth)acrylate, propyleneglycol di(meth)acrylate, polypropyleneglycol (meth)acrylate, butanediol di(meth)acrylate, butyleneglycol di(meth)acrylate, diethyleneglycol di(meth)acrylate, hexanediol di(meth)acrylate, triethyleneglycol di(meth)acrylate, tripropyleneglycol di(meth)acrylate, tetraethyleneglycol di(meth)acrylate, dipentaerythrytol pentaacrylate, glycerin tri(meth)acrylate, pentaerythrytol tetraacrylate, triarylamine, ethyleneglycol diglycidyl ether, propylene glycol, glycerin, or ethylene carbonate may be used alone or in combinations of two or more, but not limited thereto.

Such an internal cross linking agent may be added in the concentration of about 0.001 to 1 wt % to the monomer composition. That is, if the concentration of the internal cross linking agent is too low, absorption speed of the polymer may become slow, and gel strength may become weak. To the contrary, if the concentration of the internal cross linking agent is too high, absorption power of the polymer may be lowered, and thus, it may not be preferable as an absorber.

Besides, the monomer composition may further comprise additives such as a thicker, a plasticizer, a preservative stabilizer, an antioxidant, and the like.

And, the monomer composition may be prepared in the form of a solution wherein the above explained raw materials including monomers, polymerization initiators, an internal cross linking agent, and the like are dissolved in a solvent.

Wherein, the solvent that can be used is not specifically limited as long as it can dissolve the above explained raw materials. For example, the solvent may include water, ethanol, ethyleneglycol, diethyleneglycol, triethyleneglycol, 1,4-butanediol, propyleneglycol, ethyleneglycol monobutyl ether, propyleneglycol monomethyl ether, propyleneglycol monomethyl ether acetate, methyl ethyl ketone, acetone, methyl amyl ketone, cyclohexanone, cyclopentanone, diethyleneglycol monomethylether, diethyleneglycol ethyl ether, toluene, xylene, burytolactone, carbitol, methylcellosolve acetate, N,N-dimethylacetamide, or a mixture thereof, and the like.

And, the formation of hydrous gel phase polymer through the polymerization of the monomer composition may be conducted by common polymerization methods, and the process is not specifically limited. As non-limiting examples, the polymerization method is largely classified into thermal polymerization and photo polymerization according to the kind of polymerization energy source, in case the thermal polymerization is progressed, it may be progressed in a reactor having a stirring axis such as a kneader, and in case the photo polymerization is progressed, it may be progressed in a reactor equipped with a movable conveyer belt.

For example, the monomer composition may be introduced into a reactor having a stirring axis such as a kneader, and hot air may be supplied thereto or the reactor may be heated to conduct thermal polymerization, thus obtaining hydrous gel phase polymer. At this time, the hydrous gel phase polymer discharged to the outlet of the reactor may be obtained as particles of a few millimeters to a few centimeters according to the shape of the stirring axis in the reactor. Specifically, the obtained hydrous gel phase polymer may be obtained in various forms according to the concentration of the introduced monomer composition and the introduction speed and the like, and commonly, hydrous gel phase polymer having a (weight average) particle diameter of 2 to 50 mm may be obtained.

And, for another example, in case photo polymerization of the monomer composition is progressed in a reactor equipped with a movable conveyer belt, hydrous gel phase polymer in the form of a sheet may be obtained. Wherein, the thickness of the sheet may vary according to the concentration of the introduced monomer composition and the introduction speed, but in order to secure production speed while uniformly polymerizing the whole sheet, commonly, it is preferable the thickness is controlled to a thickness of 0.5 to 5 cm.

The hydrous gel phase polymer formed by the above method may exhibit moisture content of about 40 to 80 wt %. Wherein, the moisture content is a weight occupied by moisture in the total weight of the polymer, and it may obtained by subtracting the weight of dried state polymer from the weight of hydrous gel phase polymer. Specifically, it may be defined as a value calculated by measuring weight decrease according to moisture evaporation in the polymer during the process of raising the temperature of polymer through infrared heating to dry. Wherein, the drying condition may include raising the temperature from room temperature to about 180° C. and then maintaining 180° C., and the total drying time may be set as 20 minutes including 5 minutes of the temperature rising step.

Step of drying the hydrous gel phase polymer (Step 2)

Meanwhile, the method for preparing super absorbent polymer comprises a step of drying the hydrous gel phase polymer prepared through the above explained step.

The method, if necessary, may further comprise a step of milling (coarse milling) the hydrous gel phase polymer before drying, in order to increase the efficiency of the drying step.

As non-limiting examples, mills that can be used for coarse milling may include a vertical pulverizer, a turbo cutter, a turbo grinder, a rotary cutter mill, a cutter mill, a disc mill, a shred crusher, a crusher, a chopper, a disc cutter, and the like.

The coarse milling may be conducted such that the particle diameter of the hydrous gel phase polymer may become 2 to 10 mm. That is, in order to increase drying efficiency, it is preferable that the hydrous gel phase polymer is milled to particles of 10 mm or less. However, since excessive milling could generate aggregation of particles, it is preferable that the hydrous gel phase polymer is milled to particles of 2 mm or more.

And, as such, in case the coarse milling step is passed before the drying step of the hydrous gel phase polymer, since the polymer is in the state of high moisture content, adherence of the polymer to the surface of the mill may occur. In order to minimize such a phenomenon, in the coarse milling step, fine particle aggregation inhibitors such as steam, water, surfactants, clay or silica, and the like; thermal polymerization initiators such as persulfate based initiators, azo based initiators, hydrogen peroxide and ascorbic acid; cross linking agents such as an epoxy based cross linking agent, a diol type cross linking agent, a cross linking agent containing difunctional or trifunctional or multifunctional acrylate, a monofunctional compound containing a hydroxyl group may be added, as necessary.

Meanwhile, the drying of the hydrous gel phase polymer immediately after the coarse milling or polymerization may be conducted at a temperature of 120 to 250° C., or 150 to 200° C., or 160 to 180° C. (wherein, the temperature may be defined as a temperature of heating medium supplied for drying, or a temperature of the inside of the drying reactor including heating medium and polymer in the drying process). That is, as the drying temperature is lower and the drying time is longer, the properties of the final polymer may be degraded, and in order to prevent this, it is preferable that the drying temperature is 120° C. or more. And, if the drying temperature is unnecessarily high, only the surface of hydrous gel phase polymer may be dried to generate a lot of fine particles in the milling process as described below, and the properties of the final polymer may be degraded, and in order to prevent this, it is preferable that the drying temperature is 250° C. or less.

And, as explained in the above Step 1, since the drying temperature is a temperature capable of decomposing the second thermal polymerization initiator, in the drying process, the second thermal polymerization initiator is decomposed to form radicals, thus additionally polymerizing non-reacted monomers remaining in the hydrous gel phase polymer, thereby reducing the content of non-reacted monomers in the finally prepared super absorbent polymer.

Wherein, the drying time is not specifically limited in the drying step, but it may be controlled to 20 to 90 minutes under the above drying temperature, considering process efficiency and the like.

And, a drying method in the drying step may be applied without specific limitations to the constructions, as long as it can be commonly used as a drying process of hydrous gel phase polymer. Specifically, in the drying step, hot air supply, infrared irradiation, microwave irradiation, or UV irradiation and the like may be applied.

Thus dried polymer may exhibit moisture content of about 0.1 to 10 wt %. That is, if the moisture content of polymer is less than 0.1 wt %, due to excessive drying, increase in manufacturing cost and degradation of crosslinked polymer may occur, which is not favorable. And, if the moisture content of polymer is greater than 10 wt %, faulty may be generated in the subsequent process, which is not preferable.

Step of milling the dried polymer (Step 3)

Meanwhile, the method for preparing super absorbent polymer comprises a step of milling the polymer dried through the above explained step.

The milling step is to optimize the surface area of dried polymer, and it may be conducted such that the particle diameter of the milled polymer may become 150 to 850 µm. Mills that can be used to mill to the particle diameter range may include a pin mill, a hammer mill, a screw mill, a roll mill, a disc mill, a jog mill, and the like.

And, in order to manage the properties of super absorbent polymer finally made into products, a step of selectively classifying the particles having particle diameters of 150 to 850 μm in the polymer powder obtained through the milling step may be further conducted.

Meanwhile, if necessary, the method for preparing super absorbent polymer may further comprise a step of surface cross-linking the polymer milled through the above explained step.

The surface cross-linking is a method of increasing the cross-linking density of the surface of the polymer particles, and it may be conducted by mixing a solution containing a cross linking agent (surface cross linking agent) and the milled polymer to progress a cross-linking reaction.

Wherein, the kind of the cross-linking agent (surface cross-linking agent) included in the surface cross-linking solution is not specifically limited. As non-limiting examples, the surface cross-linking agent may be one or more compound selected from the group consisting of ethyleneglycol diglycidyl ether, polyethyleneglycol diglycidyl ether, glycerol polyglycidyl ether, propyleneglycol diglycidyl ether, polypropylene glycol diglycidyl ether, ethylene carbonate, ethylene glycol, diethylene glycol, propylene glycol, triethylene glycol, tetra ethylene glycol, propane diol, dipropylene glycol, polypropylene glycol, glycerin, polyglycerin, butane diol, hetane diol, hexane diol, trimethylol propane, pentaerythrytol, sorbitol, calcium hydroxide, magnesium hydroxide, aluminum hydroxide, iron hydroxide, calcium chloride, magnesium chloride, aluminum chloride, and iron chloride.

Wherein, the content of the surface cross-linking agent may be appropriately controlled according to the kind of the cross-linking agent or reaction conditions, and the like, and preferably, it may be controlled to 0.001 to 5 parts by weight based on 100 parts by weight of the milled polymer. If the content of the surface cross-linking agent is too low, surface cross-linking may not be appropriately introduced, thus degrading the properties of the final polymer. To the contrary, if the surface cross-linking agent is excessively used, due to the excessive surface cross-linking reaction, absorption force of the polymer may decrease, which is not preferable.

Meanwhile, in order to conduct the surface cross-linking reaction, a method of introducing a surface cross-linking solution and milled polymer in a reactor and mixing them, a method of spraying a surface cross-linking solution to milled polymer, a method of continuously supplying milled polymer and surface cross-linking solution in a continuously operated mixer to mix them, and the like may be used.

And, when the surface cross-linking solution is added, water may be additionally added. As such, by adding water together, uniform dispersion of the cross-linking agent may be induced, agglomeration of polymer powder may be prevented, and the penetration depth of the surface cross-linking agent to polymer powder may be more optimized. Taking these objects and effects into consideration, the content of added water may be controlled to 0.5 to 10 parts by weight, based on 100 parts by weight of the milled polymer.

And, the surface cross-linking reaction step may be progressed at a temperature of 100 to 250° C., and it may be continuously conducted after the drying and milling steps that are progressed at relatively high temperature. Wherein, the surface cross-linking reaction may be progressed for 1 to 120 minutes, or 1 to 100 minutes, or 10 to 60 minutes. That is, in order to induce the minimum surface cross-linking reaction and to prevent damage of polymer particles and the resulting degradation of the properties due to excessive reaction, it may be progressed under the above explained surface cross-linking reaction conditions.

Advantageous Effects

The method for preparing super absorbent polymer according to the present invention may reduce the content of non-reacted monomers in super absorbent polymer, by using three kinds of polymerization initiators.

DETAILED DESCRIPTION OF THE EMBODIMENTS

Hereinafter, the preferred Examples are provided for better understanding of the invention. However, these Examples are given for illustrative purposes only and not intended to limit the scope of the present invention.

EXAMPLE 1

100 g of acrylic acid, 0.34 g of polyethylene glycol diacrylate (Mw=523) as a cross-linking agent, 0.008 g of diphenyl(2,4,6-trimethylbenzoyl)-phosphine oxide as a UV initiator, 121.5 g of 32% caustic soda (NaOH), 0.200 g of sodium persulfate, 0.060 g of 2,5-dimethyl-2,5-bis(tetrabutylperoxy)hexane, and 36.6 g of water were mixed to prepare a composition having a monomer concentration of 46 wt %.

The composition was introduced into the feed section of a polymerization reactor consisting of continuously moving conveyer belt, and irradiated by UV for 2 minutes with a UV irradiation apparatus (irradiation amount: 2 mW/cm$^2$) to progress a polymerization reaction, thus obtaining hydrous gel phase polymer as a product.

The hydrous gel phase polymer was transferred to a cutter, and then, cut to 0.2 cm. At this time, the moisture content of the cut hydrous gel phase polymer was 50 wt %. Subsequently, the hydrous gel phase polymer was dried in a hot air drier of 190° C. for 40 minutes, and the dried hydrogel polymer was milled with a pin mill. Subsequently, the polymer having an average particle diameter of 150 μm to 850 μm was classified using a sieve.

EXAMPLE 2

Super absorbent polymer was prepared by the same method as Example 1, except that 0.048 g of tert-butyl hydroperoxide was used instead of 0.060 g of 2,5-dimethy-2,5-bis(tetrabutylperoxy)hexane.

Comparative Example

Super absorbent polymer was prepared by the same method as Example 1, except that 0.060 g of 2,5-dimethy-2,5-bis(tetrabutylperoxy)hexane was not used.

Experimental Example

The super absorbent polymers prepared in the Examples and Comparative Example were assessed by the following method.

1) CRC (CRC, Centrifuge Retention Capacity)

According to EDANA method WSP 241.2, centrifuge retention capacities of the polymers of the Examples and Comparative Example were measured.

Specifically, W (g) (about 0.2 g) of each polymer obtained through the Examples and Comparative Example was uniformly put in an envelope made of non-woven fabric and the envelope was sealed, and then, impregnated in a saline solution (0.9 wt %) at room temperature. After about 30 minutes, moisture was taken out from the envelope using a centrifuge under 250 G condition for 3 minutes, and the weight W2 (g) of the envelope was measured. And, the same operation was made without using polymer, and then, the weight W1 (g) was measured. Using each obtained weight, CRC (g/g) was calculated according to the following Equation.

$$CRC(g/g)=\{(W2-W1)/W\}-1 \quad \text{[Equation 1]}$$

2) Remaining Monomer Content

According to EDANA method WSP 210.3, the remaining monomer contents of the polymers of Examples and Comparative Example were measured.

Specifically, 1 g of the polymer respectively prepared in Examples and Comparative Example was stirred at 250 rpm for 1 hour in a beaker containing a 2.5 cm spin bar in 200 mL of a saline solution (0.9 wt %) at room temperature to extract non-reacted acrylic acid. The amount of the extracted solution was analyzed by LC (liquid chromatography) to measure the amount of remaining acrylic acid.

3) Water Soluble Components

According to EDANA method WSP 270.3, the contents of water soluble components of the polymers of Examples and Comparative Example were measured.

Specifically, 1 g of the polymer respectively prepared in Examples and Comparative Example was stirred at 250 rpm for 16 hours in a beaker containing a 2.5 cm spin bar in 200 mL of a saline solution (0.9 wt %) at room temperature to extract non-reacted acrylic acid. The extracted solution was analyzed by titration to measure the amount of the extracted water soluble components.

The results are shown in the following Table 1.

TABLE 1

|  | CRC (g/g) | Remaining monomers (ppm) | Water soluble components (%) |
|---|---|---|---|
| Example 1 | 38.7 | 302 | 11.88 |
| Example 2 | 42.6 | 303 | 15.43 |
| Comparative Example | 39.4 | 396 | 12.44 |

As shown in the Table 1, although there were no significant differences between the super absorbent polymers prepared in Examples and Comparative Example with respect to CRC, it was confirmed that the remaining monomers in the super absorbent polymers prepared in Examples were remarkably reduced compared to Comparative Example.

Therefore, the super absorbent polymer according to the present invention may substantially maintain the properties of super absorbent polymer, and simultaneously, reduce the content of remaining monomers.

The invention claimed is:

1. A method for preparing super absorbent polymer comprising the steps of:
   1) polymerizing a monomer composition comprising a water soluble ethylene-based unsaturated monomer, a photopolymerization initiator, a first thermal polymerization initiator with a decomposition temperature of 40 to 120° C., and a second thermal polymerization initiator with a decomposition temperature of 120 to 250° C. to prepare a hydrous gel phase polymer,
   2) drying the hydrous gel phase polymer, and
   3) milling the dried polymer
   wherein the second thermal polymerization initiator is decomposed to form radicals, thus additionally polymerizing non-reacted monomers remaining in the hydrous gel phase polymer in the drying process.

2. The method for preparing super absorbent polymer according to claim 1, wherein the water soluble ethylene-based unsaturated monomer is a compound represented by the following Chemical Formula 1:

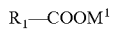

[Chemical Formula 1]

wherein, $R^1$ is an alkyl group having 2 to 5 carbon atoms, containing an unsaturated bond, and $M^1$ is a hydrogen atom, a monovalent or divalent metal, an ammonium group, or an organic amine salt.

3. The method for preparing super absorbent polymer according to claim 1, wherein the water soluble ethylene-based unsaturated monomer includes one or more selected from the group consisting of anionic monomers, non-ionic hydrophilic monomers, and amino group-containing unsaturated monomers.

4. The method for preparing super absorbent polymer according to claim 3, wherein the anionic monomers include one or more selected from the group consisting of acrylic acid, methacrylic acid, maleic anhydride, fumaric acid, crotonic acid, itaconic acid, 2-acryloylethane sulfonic acid, 2-methacryloylethane sulfonic acid, 2-(metha)acryloylpropane sulfonic acid, or 2-(meth)acrylamide-2-methyl propane sulfonic acid, or salts thereof.

5. The method for preparing super absorbent polymer according to claim 3, wherein the non-ionic hydrophilic monomers include one or more selected from the group consisting of (meth)acrylamide, N-substituted (meth)acrylate, 2-hydroxyethyl(meth)acrylate, 2-hydroxypropyl (meth)acrylate, methoxypolyethyleneglycol (meth)acrylate, or polyethyleneglycol (meth)acrylate.

6. The method for preparing super absorbent polymer according to claim 3, wherein the amino group-containing unsaturated monomers include one or more selected from the group consisting of (N,N)-dimethylaminoethyl (meth) acrylate or (N,N)-dimethylaminopropyl (meth)acrylamide, or quaternized products thereof.

7. The method for preparing super absorbent polymer according to claim 1, wherein the photopolymerization initiator is one or more selected from the group consisting of benzoin ether, dialkylacetophenone, hydroxyl alklyketone, phenylglyoxylate, benzyldimethylketal, acylphosphine and alpha-aminoketone.

8. The method for preparing super absorbent polymer according to claim 1, wherein the first thermal polymerization initiator is one or more selected from the group consisting of sodium persulfate, potassium persulfate, ammonium persulfate, 2,2-azobis-(2-midinopropane) dihydrochloride, 2,2-azobis-(N,N-dimethylene)isobutyramidine dihydrochloride, 2-(carbamoylazo)isobutyronitrile, 2,2-azobis[2-(2-imidazolin-2-yl]propane dihydrochloride, and 4,4-azobis-(4-cyanovaleric acid).

9. The method for preparing super absorbent polymer according to claim 1, wherein the second thermal polymerization initiator is a compound represented by the following Chemical Formula 2:

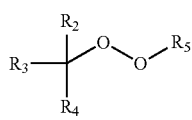

[Chemical Formula 2]

wherein, $R_2$ and $R_3$ are each independently $C_{1-4}$ alkyl, $R_4$ is $C_{1-4}$ alkyl, $C_{3-6}$ cycloalkyl, $C_{3-6}$ cycloalkyl substituted with $C_{1-4}$ alkyl, tert-butyl, hexyl, or hexyl substituted with methyl, $R_5$ is hydrogen, or $CR_6R_7R_8$, $R_6$ and $R_7$ are each independently $C_{1-4}$ alkyl, and $R_8$ is $C_{1-6}$ alkyl, $C_{1-6}$ alkyl substituted with $C_{1-4}$ alkylperoxy, or $C_{6-10}$ aryl.

10. The method for preparing super absorbent polymer according to claim 9, wherein $R_2$ and $R_3$ are methyl.

11. The method for preparing super absorbent polymer according to claim 9, wherein $R_4$ is tert-butyl, hexyl, or hexyl substituted with methyl.

12. The method for preparing super absorbent polymer according to claim 9, wherein $R_6$ and $R_7$ are methyl.

13. The method for preparing super absorbent polymer according to claim 9, wherein $R_8$ is methyl, isopentyl substituted with tert-butylperoxy, or phenyl.

14. The method for preparing super absorbent polymer according to claim 9, wherein the compound represented by the Chemical Formula 2 is 2,5-dimethyl-2,5-bis(tert-butylperoxy) hexane, tert-butyl hydroperoxide, tert-butyl cumyl peroxide, di-tert-butyl peroxide, or p-menthane hydroperoxide.

15. The method for preparing super absorbent polymer according to claim 9, wherein $R_4$ is $C_{1-4}$ alkyl, $C_{3-6}$ cycloalkyl, or $C_{3-6}$ cycloalkyl substituted with $C_{1-4}$ alkyl.

16. The method for preparing super absorbent polymer according to claim 1, further comprising the step of milling the hydrous gel phase polymer to a particle diameter of 2 to 10 mm, between the step 1 and the step 2.

17. The method for preparing super absorbent polymer according to claim 1, wherein the drying of the step 2 is conducted at a temperature of 120 to 150° C.

18. The method for preparing super absorbent polymer according to claim 1, wherein the milling of the step 3 is conducted such that the particle diameter of the milled polymer becomes 150 to 850 μm.

* * * * *